US006540657B2

(12) United States Patent
Cross, III et al.

(10) Patent No.: US 6,540,657 B2
(45) Date of Patent: Apr. 1, 2003

(54) APPARATUS AND METHOD FOR INTERNALLY INDUCING A MAGNETIC FIELD IN AN ANEURYSM TO EMBOLIZE ANEURYSM WITH MAGNETICALLY-CONTROLLABLE SUBSTANCE

(75) Inventors: DeWitte T. Cross, III, Clayton, MO (US); Stephen C. Porter, Fremont, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 123 days.

(21) Appl. No.: 09/752,749

(22) Filed: Dec. 28, 2000

(65) Prior Publication Data

US 2002/0087044 A1 Jul. 4, 2002

(51) Int. Cl.[7] ........................... A61M 37/00; A61N 2/00
(52) U.S. Cl. ....................................................... 600/12
(58) Field of Search ...................... 600/12, 13, 11, 600/9, 433, 435; 424/9; 604/93.01, 95.03, 264, 523

(56) References Cited

U.S. PATENT DOCUMENTS

| | | | | |
|---|---|---|---|---|
| 5,108,359 A | * | 4/1992 | Granov et al. | 128/898 |
| 5,122,136 A | * | 6/1992 | Guglielmi et al. | 600/585 |
| 5,236,410 A | * | 8/1993 | Granov et al. | 128/898 |
| 5,250,071 A | | 10/1993 | Palermo | |
| 5,855,578 A | * | 1/1999 | Guglielmi et al. | 606/108 |
| 6,010,498 A | * | 1/2000 | Guglielmi | 606/108 |
| 6,014,580 A | | 1/2000 | Blume et al. | |
| 6,123,714 A | | 9/2000 | Gia et al. | |
| 6,296,622 B1 | * | 10/2001 | Kurz et al. | 604/93.01 |
| 6,315,709 B1 | * | 11/2001 | Garibaldi et al. | 600/12 |
| 6,364,823 B1 | * | 4/2002 | Garibaldi et al. | 600/12 |
| 6,375,606 B1 | * | 4/2002 | Garibaldi et al. | 600/12 |

FOREIGN PATENT DOCUMENTS

| | | |
|---|---|---|
| EP | 1 005 837 A | 6/2000 |
| JP | 04 312454 A | 11/1992 |
| WO | WO00 54832 A | 9/2000 |
| WO | WO00 54835 A | 9/2000 |
| WO | WO01 15608 A | 3/2001 |

* cited by examiner

Primary Examiner—Gene Mancene
Assistant Examiner—Arnold Castro
(74) Attorney, Agent, or Firm—Bingham McCutchen LLP

(57) ABSTRACT

The present invention involves a magnetic detachable embolization apparatus and method for embolizing an aneurysm of a blood vessel. The apparatus includes an element adapted to be detachably connected to a distal portion of a catheter for insertion within an aneurysm of a blood vessel, the element being shaped to be retained within the aneurysm, and one or more magnets carried by the element to internally induce a magnetic field from within the aneurysm to control a magnetic field controllable embolic to embolize the aneurysm. The method includes providing a magnetic-field controllable embolic within or adjacent to an aneurysm in a blood vessel, and internally inducing a magnetic field from within the aneurysm to control the magnetic-field controllable embolic to embolize the aneurysm.

49 Claims, 5 Drawing Sheets

U.S. 6,540,657 B2

APPARATUS AND METHOD FOR INTERNALLY INDUCING A MAGNETIC FIELD IN AN ANEURYSM TO EMBOLIZE ANEURYSM WITH MAGNETICALLY-CONTROLLABLE SUBSTANCE

FIELD OF THE INVENTION

The invention relates, in general, to an apparatus and method for forming an occlusion in a mammalian body, and, in particular to an apparatus and method for internally inducing a magnetic field in an aneurysm to embolize the aneurysm with a magnetically-controllable substance.

BACKGROUND

Like all parts of the body, the brain is composed of living cells that require a blood supply to provide oxygen and nutrients. A hemorrhage in a blood vessel in the brain or in the space closely surrounding the brain is a common cause of strokes. Hemorrhage refers to bleeding into the brain, usually because of a problem with a blood vessel. The problem is often an aneurysm.

An aneurysm is an abnormal bulging outward of blood vessel wall. The wall may smoothly bulge outward in all directions (a fusiform aneurysm) or it may form a sack arising from one wall (a saccular aneurysm). If the aneurysm ruptures, a hemorrhage occurs. This can compress and irritate the surrounding blood vessels, resulting in a reduced supply of oxygen and nutrients to the cells, possibly causing a stroke.

Aneurysms can be treated from outside the blood vessel using surgical techniques or from inside the blood vessel using endovascular techniques. Endovascular treatment of an aneurysm is performed using a catheter. X-ray, magnetic resonance imaging (MRI) equipment, or other visualization equipment may be used to view the progress during the procedure.

A magnetically directable embolic such as an acrylic, iron-containing glue has been proposed to fill or obliterate aneurysms. The embolic is delivered by means of a catheter and is directed into an aneurysm with an external magnetic field generated by a permanent magnet or electrogmanetic device used for Stereotaxis prcedures such as a prototype device made by Stereotaxis Inc. of St. Louis, Mo. An example of such a device is shown and described in U.S. Pat. No. 6,014,580 to Blume, et al. Problems with this approach include that the Stereotaxis machine is cumbersome and expensive and, in some cases, the external magnetic field produced by the Stereotaxis machine is not strong enough to control delivery of the iron-containing, magnetically-directable glue into the aneurysm.

SUMMARY OF THE INVENTION

An aspect of the present invention involves a magnetic detachable embolization apparatus for embolizing an aneurysm of a blood vessel. The apparatus includes an element adapted to be detachably connected to a distal portion of a catheter for insertion within an aneurysm of a blood vessel, the element being shaped to be retained within the aneurysm, and one or more magnets carried by the element to internally induce a magnetic field from within the aneurysm to control a magnetic field controllable embolic to embolize the aneurysm. The one or more magnets may be one or more permanent magnets or electromagnets.

An additional aspect of the present invention involves a method for embolizing an aneurysm of a blood vessel. The method includes providing a magnetic-field controllable embolic at an aneurysm in a blood vessel, and internally inducing a magnetic field at the aneurysm site to control the magnetic-field controllable embolic to embolize the aneurysm.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the present invention, in which similar elements are referred to by common reference numerals.

DETAILED DESCRIPTION OF THE PREFERRED EMBODIMENTS

Figure 1:
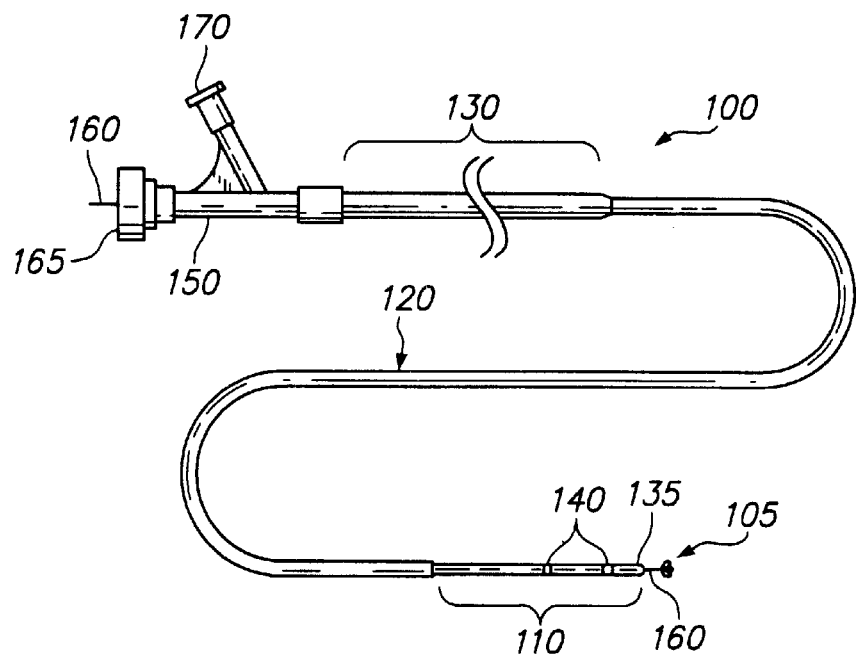
FIG. 1 is a side-elevational view of an embodiment of a catheter that may be used with the magnetic detachable embolization apparatus.

With reference to FIG. 1, an exemplary multi-section catheter 100 that may be used to deliver and deploy a magnetic detachable embolization apparatus 105, which is constructed in accordance with an embodiment of the invention, at a targeted aneurysm 107 (FIG. 2) will now be described. Although the invention will be described in terms of aneurysm treatment, it may also be adaptable for endovascular occlusion in arteries, veins, vascular malformations, and arteriovenous fistulas. The invention may also be used for forming an occlusion in other areas of a mammalian body.

The catheter 100 includes a distal section 110, an intermediate section 120, and a proximal section 130. The sections decrease in flexibility from the proximal section 130 to the distal section 110.

The distal section 110 is very flexible and soft to allow deep penetration into the extraordinary convolutions of the neurological vasculature without trauma. The magnetic detachable embolization apparatus 105 is deployed from the distal section 110 of the catheter 100 at a distal end 135. The distal section 110 may include one or more radio-opaque bands 140 to allow viewing of the position of the distal section under fluoroscopy.

A luer assembly 150 at the proximal section 130 of the catheter 100 accomodates a core, utility, pusher, or guide wire 160. The wire 160 may be made of any well-known guide wire material in the art such as stainless steel. The magnetic detachable embolization apparatus 105 may be attached to a distal end of the wire 160. The luer assembly 150 may also include a fluid port for introducing and/or removing a magnetically controllable embolization substance and a power port 170 for connecting the catheter 100 to a power supply. The catheter 100 may also include any well-known steering assembly in the art for delivering the magnetic detachable embolization apparatus 105 to the targeted aneurysm 107.

Figure 2:
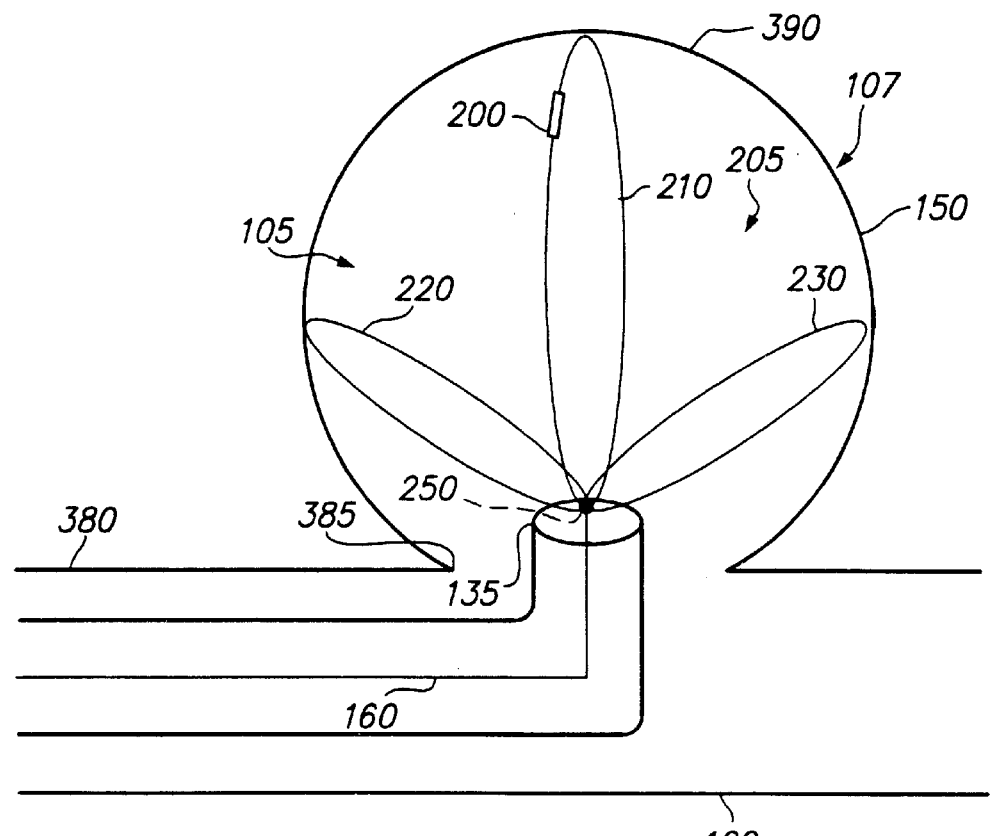
FIG. 2 is a side-elevational view of a distal portion of the catheter illustrated in FIG. 1 in a blood vessel with an embodiment of a magnetic detachable embolization apparatus shown disposed in an aneurysm.

With reference to FIG. 2, an embodiment of the magnetic detachable embolization apparatus 105 will now be described. The apparatus 105 includes one or more permanent Neodynium (NdFeB) or Samarium Cobalt (SmCo) magnets 200 attached to an element shaped to retain or secure the apparatus 105 within the aneurysm 107. In the embodiment shown, the element is a multi-loop assembly 205 made of a shape memory material such as Nitinol™. The multi-loop assembly 205 may be a modified TriSpan™ coil sold by Target Therapeutics® of Freemont, Calif. The multi-loop assembly 205 preferably includes three wire wings or loops, a first wire loop 210, a second wire loop 220, and a third wire loop 230. Although the assembly 205 is shown as having three wire loops, other numbers of loops may be used. The expanded wings or loops 210, 220, 230 of the multi-loop assembly 205 help to secure the device in the aneurysm 107 once the assembly 205 is deployed in the aneurysm 107.

The multi-loop assembly 205 is coupled to the wire 160 by a detachment mechanism 250. Examples of detachment mechanisms that may be used include a mechanical detachment mechanism such as that described in U.S. Pat. No. 5,250,071 ("the '71 patent") to Palermo (or the mechanical detachment mechanism described below with respect to FIG. 5) and an electrolytic detachment mechanism such as those described in U.S. Pat. No. 5,122,136 ("the '136 patent") to Guglielmi, et al. and U.S. Pat. No. 6,123,714 ("the '714 patent) to Gia, et al. The '71, '136, and '714 patents are incorporated by reference as though set forth in full. Preferably, an electrolytic detachment mechanism similar to those described in the '136 patent or the '714 patent is used. An electrolytic detachment mechanism includes an electrolytic, sacrificial joint that separates when a small electric current is applied therethrough. The '136 patent describes a soldered electrolytic, sacrificial joint and the '714 patent describes a solderless electrolytic, sacrificial joint.

Figure 3:
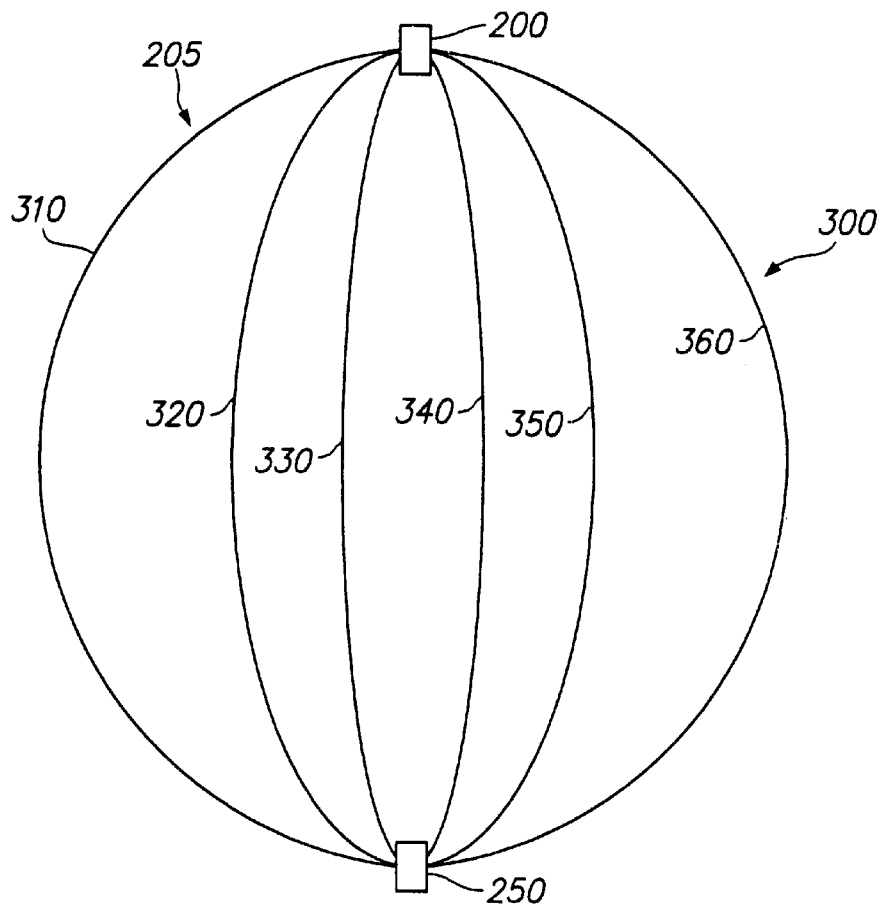
FIG. 3 is a side-elevational view of an additional embodiment of a magnetic detachable embolization apparatus.

Although the magnetic detachable embolization apparatus 105 has been described as having a multi-loop configuration, in alternative embodiments, the apparatus may include other configurations. For example, with reference to FIG. 3, the magnetic detachable embolization apparatus 105 may be comprised of a generally spherical, basket assembly 305. The basket assembly 305 includes a plurality of arced wire splines 310, 320, 330, 340, 350, 360 attached at distal ends to a permanent Neodynium (NdFeB) or Samarium Cobalt (SmCo) magnet 200 and attached at proximal ends to a detachment mechanism 250. One or more of the splines 310, 320, 330, 340, 350, 360 may carry one or more magnets 200.

The apparatus 105 may come in a variety of sizes to accommodate different size aneurysms and/or a variety of configurations to accomodate aneurysms having different shapes.

Figure 4:
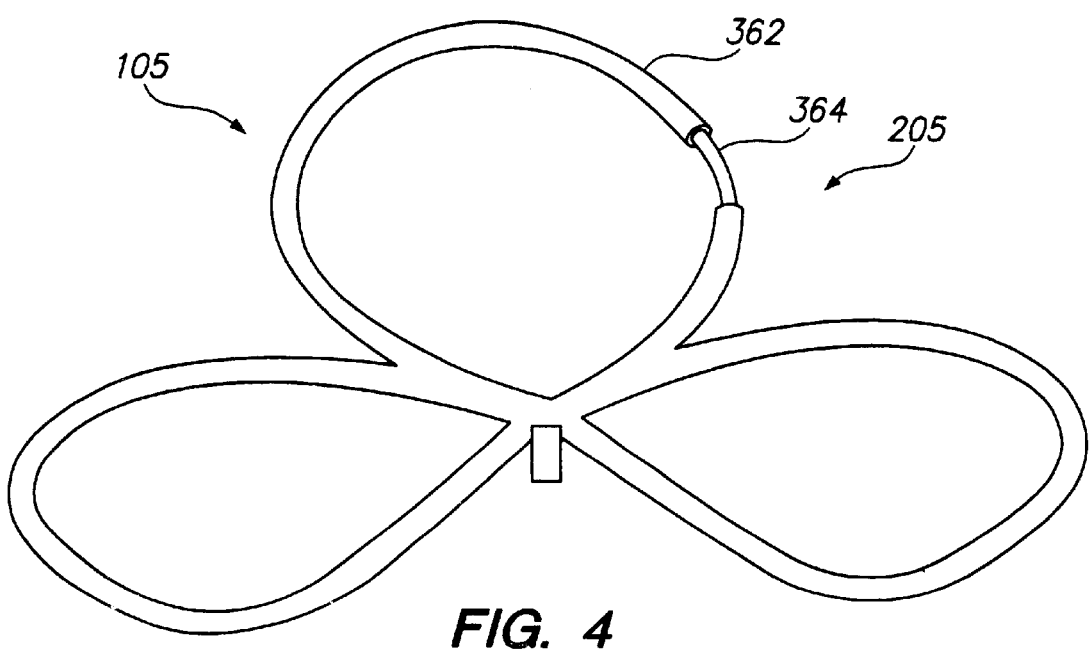
FIG. 4 is a side-elevational view of another embodiment of a magnetic detachable embolization apparatus with a polymer/magnetic-particle composite material surrounding an internal support.

With reference to FIG. 4, although the apparatus 105 has been shown as having a single magnet 200, the apparatus 105 may carry multiple magnets. For example, the multi-loop assembly 205 may be coated with a polymer and magnetic-particle composite material 362 having multiple tiny magnetic particles therein. The composite material 362 allows enhanced control over magnetic liquid embolics by distribution of the tiny magnetic particles over the entire length of the assembly 205. The composite material 362 also gives the apparatus 105 more flexibility than the embodiment shown in FIG. 2. The multi-loop assembly 205 serves as an internal support 364 that imparts shape memory to the apparatus 105.

Figure 5:
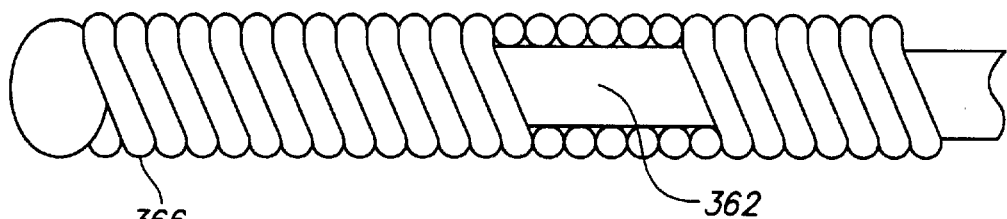
FIG. 5 is a side-elevational view of an embodiment of an external support surrounding a polymer/magnetic-particle composite material.

With reference to FIG. 5, in an alternative embodiment, an external support 366 may impart shape memory to the apparatus 105. For example, the external support 366 may be a platinum coil that surrounds the polymer/magnetic-particle composite material 362.

In a further embodiment, the apparatus 105 may include a polymer/magnetic-particle composite material 362 without an internal support 364 or external support 366. The composite material 362 may include a shape memory polymer in the composite without other support. When deployed, the composite material 362 forms an element shaped to retain or secure the apparatus 105 within the aneurysm.

In a still further embodiment, the apparatus may include the composite material 362 where the composite material 362 has no other support and does not include a shape memory.

Figure 6:
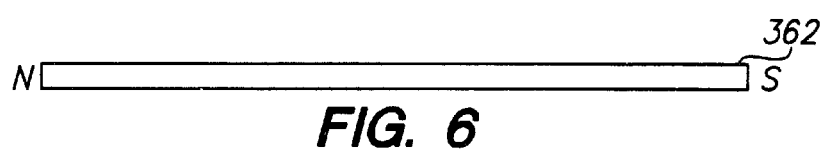
FIGS. 6–8 are exemplary illustrations of how the magnetic properties of the elongate polymer/magnetic-particle composite material may vary.
Figure 7:
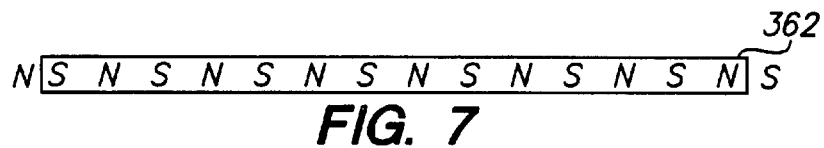
Figure 8:
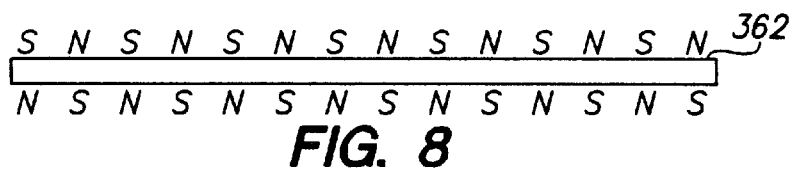

With reference to FIGS. 6–8, the magnetic properties of the composite material 362 may be varied such that the apparatus 105 exhibits single or multiple magnetic dipoles. FIG. 6 illustrates an embodiment of the composite material 362 where the material 362 includes single dipoles. FIGS. 7 and 8 illustrate embodiments of the composite material 362 where the material 362 includes multiple dipoles. In FIG. 7, the composite material 362 has multiple dipoles aligned with the longitudinal axis of the material 362. In FIG. 8, the composite material 362 has multiple dipoles aligned transversely with respect to the longitudinal axis of the material 362.

Figure 9:
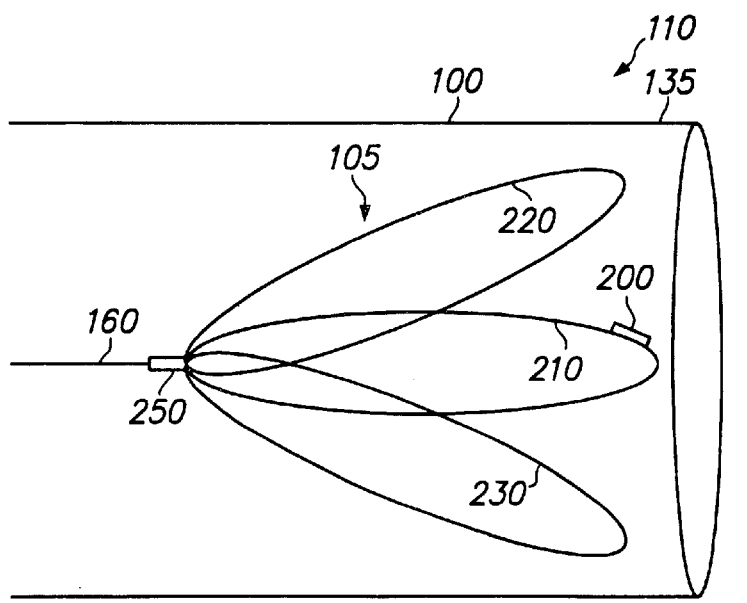
FIG. 9 is a side-elevational view of the distal portion of the catheter illustrated in FIG. 2 with the magnetic detachable embolization apparatus disposed therein in a retracted state.

With reference specifically to FIGS. 2 and 9, the magnetic detachable embolization apparatus 105 will now be described in use. The catheter 100 is introduced into the vasculature of a patient via a cannula or introducer sheath and snaked through the vasculature of the patient to the targeted aneurysm 107 by any well-known method in the art. X-ray, fluoroscopy or other well-know visualization techniques may be used to assist the physician in directing the catheter 10 to the targeted aneurysm 107. The catheter 100 may be introduced over a guide wire such as the guide wire 106 to facilitate delivery of the catheter 100 to the targeted aneurysm 107. FIG. 9 illustrates the magnetic detachable embolization apparatus 105 in a retracted or un-deployed state, which is how the apparatus 105 may be oriented as the catheter 100 is being delivered to the targeted aneurysm 107, before the apparatus 105 is deployed at the aneurysm site. The wire loops 210, 220, 230 are folded together so as to fit inside the distal portion 110 of the catheter 100. The distal end 135 of the catheter 100 may be positioned at the aneurysm site adjacent a neck 385 of the aneurysm 107, at the neck 385 of the aneurysm 107, or within the aneurysm 107.

Once the distal end 135 of the catheter 100 is delivered to the aneurysm 107, the apparatus 105 may be deployed within the aneurysm 107. This may be accomplished by advancing the guide wire 250 distally through the catheter 100. Preferably, the apparatus 105 has a pre-shaped memory so that the apparatus 105 will automatically deploy into the configuration shown in FIG. 2 when the apparatus 105 is advanced into the aneurysm 107. In an alternative embodiment, the catheter 100 may include a sheath that is retracted to deploy the apparatus 105. The apparatus 105 is preferably positioned in the aneurysm 107 so that the first wire loop 210 is positioned near a top center of a dome 390 of the aneurysm 107. The wire loops 210, 220, 230 hold the apparatus 105 securely within the aneurysm 107.

Next, a magnetically controllable embolic, preferably an acrylic, iron-containing glue, is delivered to the aneurysm 107 via the catheter 100. In an alternative embodiment, the embolic may have a different composition. The one or more permanent magnets 200 (or the polymer/magnetic-particle composite material 362 illustrated in FIGS. 4–8) of the apparatus 105 internally attracts, from within the aneurysm 107, the iron-containing embolic to the magnet(s) 200/ material 362, filling the aneurysm 107. The apparatus 105 may be detached from the wire 160 using the detachment mechanism 250 before or after the embolic is delivered to the aneurysm 107. Further, if the apparatus 105 is detached from the wire 160 after the embolic is delivered to the aneurysm 107, the apparatus 105 may be detached from the wire 160 after the embolic has sufficiently hardened or polymerized in the aneurysm 107.

The apparatus 105 is left in the aneurysm 107 and the catheter 100 is withdrawn from the patient's body. The permanent magnet(s) 200/composite material 362 may continue to attract the iron-containing embolic to the magnet(s) 200 and within the aneurysm 107 after the catheter 100 is withdrawn.

Although the magnetic detachable embolization apparatus 105 has been described as including a permanent magnet(s) 200/composite material 362, in alternative embodiments, the detachable embolization apparatus may include an electromagnet that is used to internally induce a magnetic field within the aneurysm 107 for embolizing the aneurysm 107 by running electrical current through the electromagnet.

Figure 10:
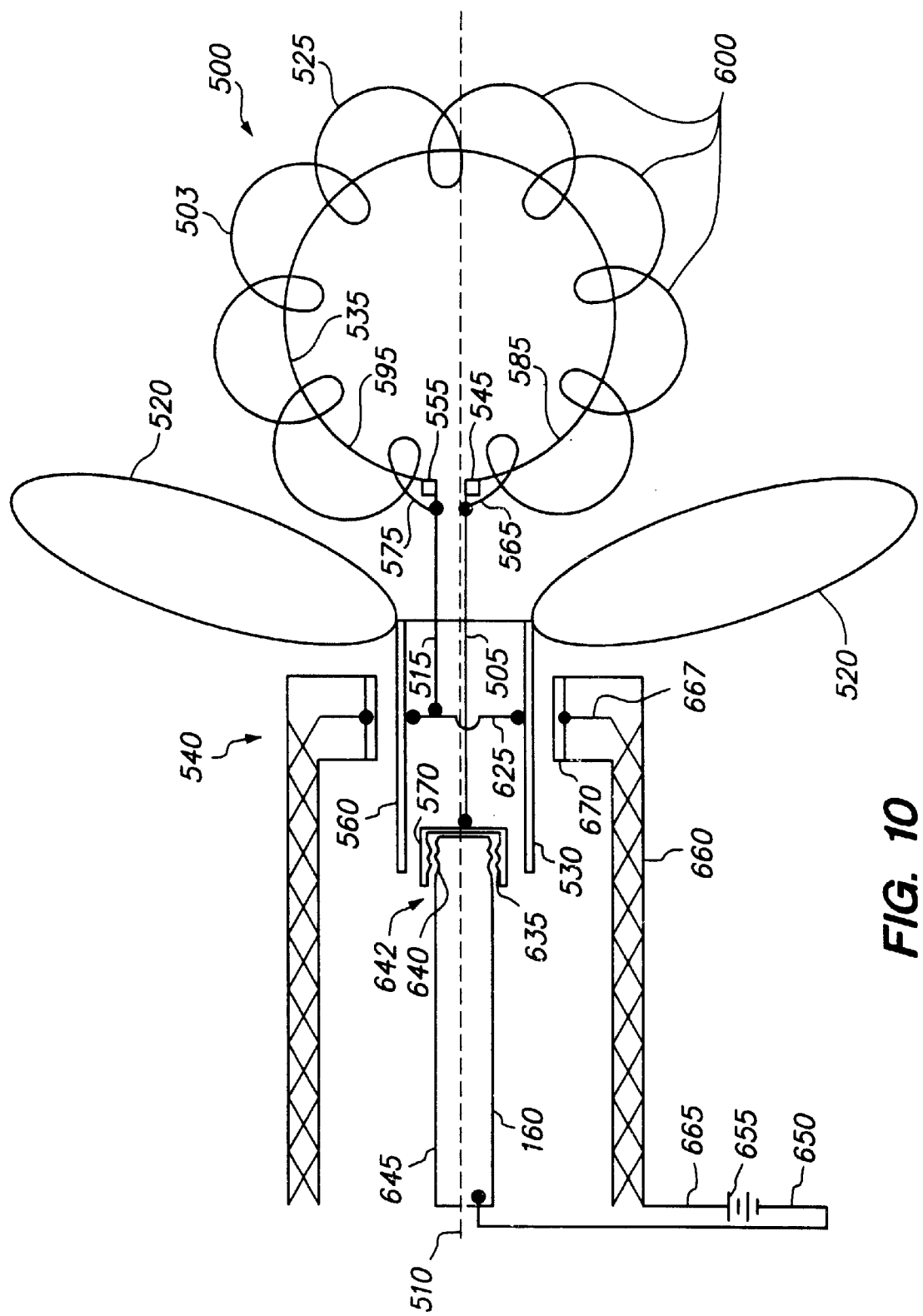
FIG. 10 is side-elevational view of a distal portion of a catheter with a further embodiment of a magnetic detachable embolization apparatus shown.

For example, with reference to FIG. 10, an embodiment of an electromagnetic detachable embolization apparatus 500 is shown. The apparatus 500 includes a curvilinear, toroid-shaped electromagnet 503 aligned with an axis 510 of the catheter 100 and a pair of wire loops 520 to help secure the apparatus 500 within the aneurysm 107. The electromagnet 503 and the wire loops 520 are coupled to a cylindrical base 530 that is configured to be slidably disposed within a distal portion 540 of the catheter 100. The cylindrical base 530 includes an outer cylindrical conductive surface 560 and an inner cylindrical conductive surface 570.

The electromagnet 503 includes a lead wire 505, a return wire 515, a main wire 525, an insulated structural support wire 535, a first insulating separator 545, and a second insulating separator 555. The lead wire 505 is electrically coupled to the inner cylindrical conductive surface 570 of the cylindrical base 530 and the return wire 515 is electrically coupled to the outer cylindrical conductive surface 560 of the cylindrical base 530. The main wire 525 has a lead end 565 electrically connected to the lead wire 505 and a return end 575 electrically connected to the return wire 515. The first insulating separator 545 connects the lead wire 505 to a first portion 585 of the insulated structural support wire 535 and the second insulating separator 555 connects the return wire 515 to a second portion 595 of the insulated structural support wire 535. The main wire 525 includes numerous coils 600 that together form the curvilinear, toroid shape of the electromagnet 503.

The cylindrical base 530 will now be described in more detail. The outer cylindrical conductive surface 560 of the cylindrical base 530 may be electrically coupled to the return wire 515 via a cylinder lead wire 625 located inside the cylinder 530. Alternatively, the return wire 515 may be coupled directly to the outer cylindrical conductive surface 560 of the cylindrical base 530. The inner cylindrical conductive surface 570 is electrically coupled to the lead wire 505 and includes internal threads 635 threadably engageable with external threads 640 of the wire 160. A proximal end 645 of the wire 160 is connected to a lead 650 of a current supply 655. This threaded coupling forms a mechanical detachment mechanism 642. The inner cylindrical conductive surface 570 is preferably integral with the the outer cylindrical conductive surface 560 of the cylindrical base 530 so as not to allow relative rotation therebetween. Insulating material may be located between the inner cylindrical conductive surface 570 and the outer cylindrical conductive surface 560. This insulating material may partially or completely fill any space inside the cylindrical base 530.

The catheter 100 may include a braided conducting wire 660 in the catheter wall. A proximal end 665 of this wire 660 may be electrically coupled to the current supply 655. A distal end 667 of the braided wire 660 is electrically coupled to a catheter contact 670. The catheter contact 670 is cylindrical and is located at the distal end of the catheter 100. The catheter contact 670 slidably receives the outer cylindrical surface 560 of the cylindrical base 530 for electrical communication therewith. The sliding friction of this connection must be great enough to hold the cylindrical base 530 in place when the wire 160 is unscrewed from the internal threads 635 of the cylindrical base 530, but small enough to allow the catheter 100 to be withdrawn from the aneurysm site without retaining the apparatus 500. In an alternative embodiment, the wire 660 and contact 670 may be incorporated within the core wire 160.

In use, the catheter 100 is snaked through the vasculature of the patient to a targeted aneurysm 107 with the electromagnetic detachable embolization apparatus 500 collapsed within the distal portion 540 of the catheter 100. The apparatus 500 is deployed within the aneurysm 107 so that the electromagnet 503 is positioned near a top center of a dome 390 of the aneurysm 107. The wire loops 520 hold the apparatus 500 securely within the aneurysm 107. Current supplied by the power source 655 flows through the electromagnet 503, electromagnetically and internally inducing a magnetic field in the aneurysm 107. Next, the a magnetically controllable embolic is delivered to the aneurysm 107 via the catheter 100. The electromagnet 503 of the apparatus 500 attracts the iron-containing embolic to the electromagnet 503, filling the aneurysm 107. Once the aneurysm 107 is filled a sufficient amount and the embolic has hardened or polymerized a sufficient amount, the distal end of the wire 160 is unscrewed from the internal threads 635 of the cylindrical base 530. The catheter 100 is withdrawn from the patient's body and the apparatus 500 is left impregnated in the hardened embolic, within the aneurysm 107.

Although the electromagnet 503 has been described above as having a toroidal, curvilinear configuration, in alternative embodiments, the electromagnet may have different configurations.

Figure 11:
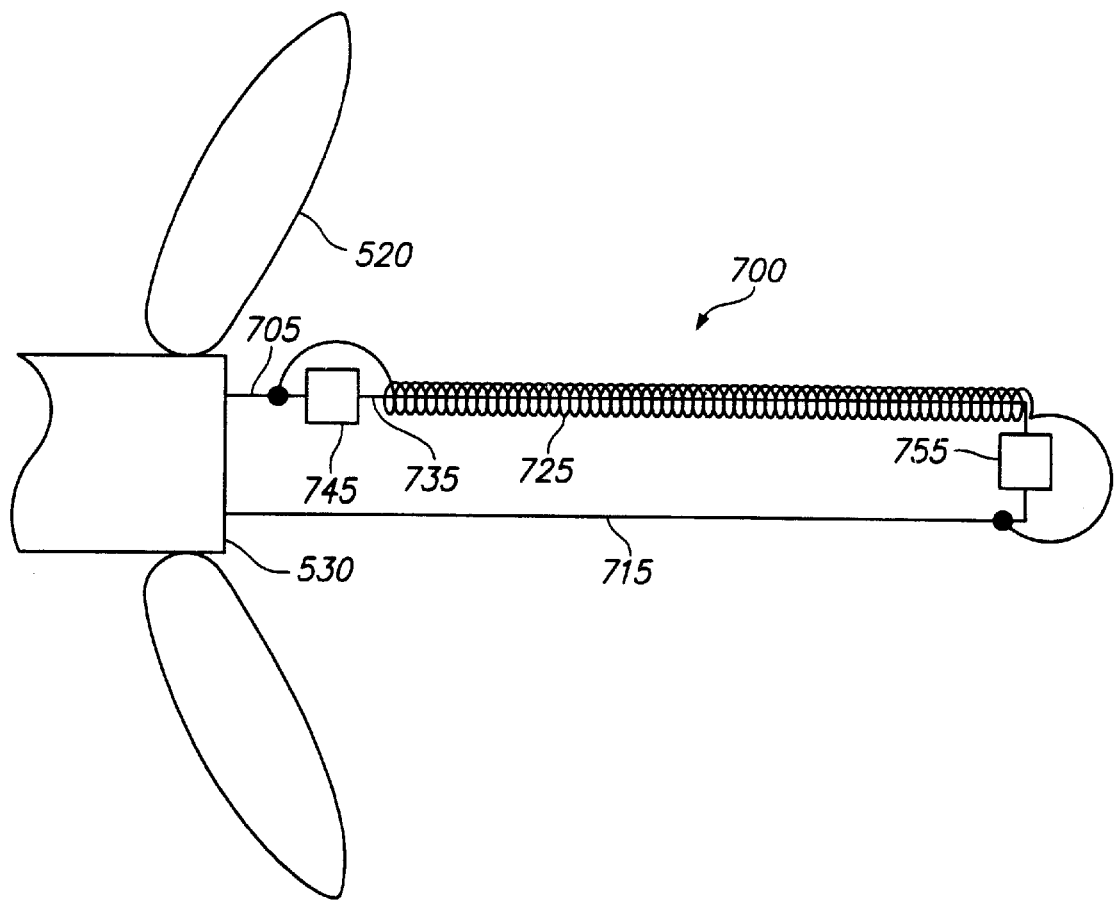
FIG. 11 is side-elevational view of a still further embodiment of a magnetic detachable embolization apparatus shown.

For example, with reference to FIG. 11, an embodiment of a linear electromagnet 700 is shown. The electromagnet 700 includes a lead wire 705, a return wire 715, a main coiled wire 725, an insulated structural support wire 735, a first insulating separator 745 that isolates the lead wire 705 from the support wire 735, and a second insulating separator 755 that isolates the return wire 715 from the support wire 735. Otherwise, the electromagnetic detachable embolization apparatus 500 is the same as that illustrated in FIG. 10.

The above-described embodiments of the invention internally induce a magnetic field, from within the aneurysm, to embolize the aneurysm with a magnetically-directable embolic. This eliminates the needs for a cumbersome and expensive superconducting electromagnetic device or large permanent magnet such as those used for Stereotaxis procedures and produces a stronger and more efficient magnetic field at the point of interest than that produced by such devices.

While embodiments and applications of this invention have been shown and described, it would be apparent to those in the field that many more modifications are possible without departing from the inventive concepts herein. The invention, therefore, is not to be restricted except in the spirit of the appended claims.

What is claimed is:

1. A magnetic detachable embolization apparatus for embolizing an aneurysm of a blood vessel, comprising:
    an element adapted to be detachably connected to a distal portion of a guide or pusher wire for insertion within an aneurysm of a blood vessel, the element shaped to be retained within the aneurysm; and
    one or more magnets carried by the element to internally induce a magnetic field from within the aneurysm to control a magnetic field controllable embolic to embolize the aneurysm.

2. The apparatus of claim 1, wherein the one or more magnets include one or more permanent magnets.

3. The apparatus of claim 2, wherein the one or more permanent magnets include one or more NdFeB or SmCo magnets.

4. The apparatus claim 2, wherein the one or more permanent magnets include a polymer and magnetic particle composite material.

5. The apparatus of claim 4, wherein the element forms an internal support for the composite material.

6. The apparatus of claim 4, wherein the element forms an external support for the composite material.

7. The apparatus of claim 4, wherein the element is the composite material.

8. The apparatus of claim 4, wherein the composite material includes single magnetic dipoles.

9. The apparatus of claim 4, wherein the composite material includes multiple magnetic dipoles.

10. The apparatus of claim 9, wherein the multiple magnetic dipoles are aligned with a longitudinal axis of the composite material.

11. The apparatus of claim 9, wherein the multiple magnetic dipoles are aligned transversely with respect to a longitudinal axis of the composite material.

12. The apparatus of claim 1, wherein the one or more magnets include an electromagnet.

13. The apparatus of claim 12, wherein the electromagnet is curvilinear.

14. The apparatus of claim 12, wherein the electromagnet is linear.

15. The apparatus of claim 1, further including a detachment mechanism for detachably mounting the guide or pusher wire to the apparatus.

16. The apparatus of claim 15, wherein the detachment mechanism is an electrolytic, sacrificial joint.

17. The apparatus of claim 15, wherein the one or more magnets is an electromagnet and the detachment mechanism includes first and second threadably engageable portions.

18. The apparatus of claim 1, wherein the element includes multiple loops of wire shaped to retain the apparatus within the aneurysm.

19. The apparatus of claim 18, wherein the one or more magnets is one or more permanent magnets carried by at least one of the loops.

20. The apparatus of claim 18, wherein the element includes a third loop of wire, and the one or more magnets is a polymer and magnetic particle composite material carried by the loops.

21. The apparatus of claim 1, wherein the element has a generally spherical basket shape.

22. The apparatus of claim 1, wherein the element includes a radio-opaque marker.

23. The apparatus of claim 1, wherein the element comes in a variety of sizes to accommodate different size aneurysms.

24. The apparatus of claim 1, wherein the element comes in a variety of configurations to accommodate different aneurysm configurations.

25. A method of embolizing an aneurysm of a blood vessel, comprising:
    providing a magnetic-field controllable embolic within or adjacent to an aneurysm in a blood vessel;
    internally inducing a magnetic field from within the aneurysm to control the magnetic-field controllable embolic to embolize the aneurysm.

26. The method of claim 25, wherein the step of internally inducing a magnetic field includes internally inducing the magnetic field with a magnetic detachable embolization apparatus including an element adapted to be detachably connected to a distal portion of a catheter for insertion within an aneurysm of a blood vessel, the element shaped to be retained within the aneurysm, and one or more magnets carried by the element to internally induce a magnetic field from within the aneurysm to control a magnetic field controllable embolic to embolize the aneurysm.

27. The method of claim 26, wherein the one or more magnets include one or more permanent magnets, and the method further includes internally inducing the magnetic field from within the aneurysm with the one or more permanent magnets.

28. The method of claim 27, wherein the one or more permanent magnets include one or more NdFeB or SmCo magnets.

29. The method of claim 27, wherein the one or more permanent magnets is a polymer and magnetic particle composite material.

30. The method of claim 29, wherein the element forms an internal support for the composite material.

31. The method of claim 29, wherein the element forms an external support for the composite material.

32. The method of claim 29, wherein the element is the composite material.

33. The method of claim 29, wherein the composite material includes single magnetic dipoles.

34. The method of claim 29, wherein the composite material includes multiple magnetic dipoles.

35. The method of claim 34, wherein the multiple magnetic dipoles are aligned with a longitudinal axis of the composite material.

36. The method of claim 34, wherein the multiple magnetic dipoles are aligned transversely with respect to a longitudinal axis of the composite material.

37. The method of claim 26, wherein the one or more magnets is an electromagnet, and the method includes internally inducing the magnetic field from within the aneurysm with the electromagnet.

38. The method of claim 37, wherein the electromagnet is curvilinear.

39. The method of claim 37, wherein the electromagnet is linear.

40. The method of claim 26, further including detaching the element from the distal portion of the catheter and leaving the element within the aneurysm.

41. The method of claim 40, wherein the step of detaching includes includes running a current through an electrolytic, sacrificial joint to separate the element from the push or guide wire.

42. The method of claim 40, wherein the one or more magnets is an electromagnet and the step of detaching includes detaching first and second threadably engageable portions.

43. The method of claim 26, wherein the element includes multiple loops of wire shaped to retain the apparatus within the aneurysm.

44. The method of claim 43, wherein the one or more magnets is one or more permanent magnets carried by at least one of the loops.

45. The method of claim 43, wherein the element includes a third loop of wire, and the one or more magnets is a polymer and magnetic particle composite material carried by the loops.

46. The method of claim 26, wherein the element has a generally spherical basket shape.

47. The method of claim 26, wherein the element includes a radio-opaque marker.

48. The method of claim 26, wherein the element comes in a variety of sizes to accommodate different size aneurysms, and the method includes determining the proper size element for a targeted aneurysm and using the determined size element in the aneurysm.

49. The method of claim 26, wherein the element comes in a variety of configurations to accommodate different aneurysm configurations, and the method includes determining the proper configuration element for a targeted aneurysm and using the determined configuration element in the aneurysm.

* * * * *